(12) United States Patent
Elliott

(10) Patent No.: US 7,488,326 B2
(45) Date of Patent: Feb. 10, 2009

(54) COMBINATION TARGETING GUIDE AND DRIVER INSTRUMENT FOR USE IN ORTHOPAEDIC SURGICAL PROCEDURES

(75) Inventor: Eric Matthew Elliott, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 740 days.

(21) Appl. No.: 10/750,787

(22) Filed: Jan. 2, 2004

(65) Prior Publication Data

US 2005/0149045 A1   Jul. 7, 2005

(51) Int. Cl.
*A61B 17/58* (2006.01)
*A61F 2/00* (2006.01)

(52) U.S. Cl. ........................................ 606/96
(58) Field of Classification Search ................ 606/53, 606/86, 96–99, 103, 104; 7/164, 165; 81/44
See application file for complete search history.

(56) References Cited

U.S. PATENT DOCUMENTS

| | | | | |
|---|---|---|---|---|
| 2,106,749 A * | 2/1938 | Knight | ........................ | 7/104 |
| 4,383,527 A * | 5/1983 | Asnis et al. | ................... | 606/96 |
| 4,450,835 A * | 5/1984 | Asnis et al. | ................... | 606/73 |
| 4,617,692 A * | 10/1986 | Bond et al. | ...................... | 7/158 |
| 4,744,353 A * | 5/1988 | McFarland | .................... | 606/96 |
| 5,588,169 A * | 12/1996 | Chuang | ......................... | 7/138 |
| 6,235,034 B1 * | 5/2001 | Bray | ............................. | 606/71 |
| 6,238,400 B1 * | 5/2001 | Bays | ............................. | 606/96 |
| 6,416,518 B1 * | 7/2002 | DeMayo | ....................... | 606/96 |
| 6,606,925 B1 * | 8/2003 | Gmeilbauer | ............... | 81/177.1 |
| 6,692,503 B2 * | 2/2004 | Foley et al. | ................... | 606/96 |
| 6,725,080 B2 * | 4/2004 | Melkent et al. | ............. | 600/424 |
| RE38,684 E * | 1/2005 | Cesarone | .................... | 606/915 |
| 6,951,154 B2 * | 10/2005 | Hsien | ............................. | 81/60 |

OTHER PUBLICATIONS

Hand Biomechanics Lab, Inc., Agee WristJack® Multiplanar Ligamenototaxis™ Fracture Reduction System Surgeons Manual Part No. 306000Q, 2002.
Acumed, External Fixation Systems, Stableloc Brochure, 1999.
Orthofix, The Pennig II Radiolucent Non-Bridging Wrist Fixator, Brochure ES-01009-SS, 2001.

* cited by examiner

*Primary Examiner*—Anu Ramana
(74) *Attorney, Agent, or Firm*—Baker & Daniels LLP

(57) ABSTRACT

The present invention provides combination targeting guide and driver instrument for use in orthopaedic surgical procedures.

7 Claims, 2 Drawing Sheets

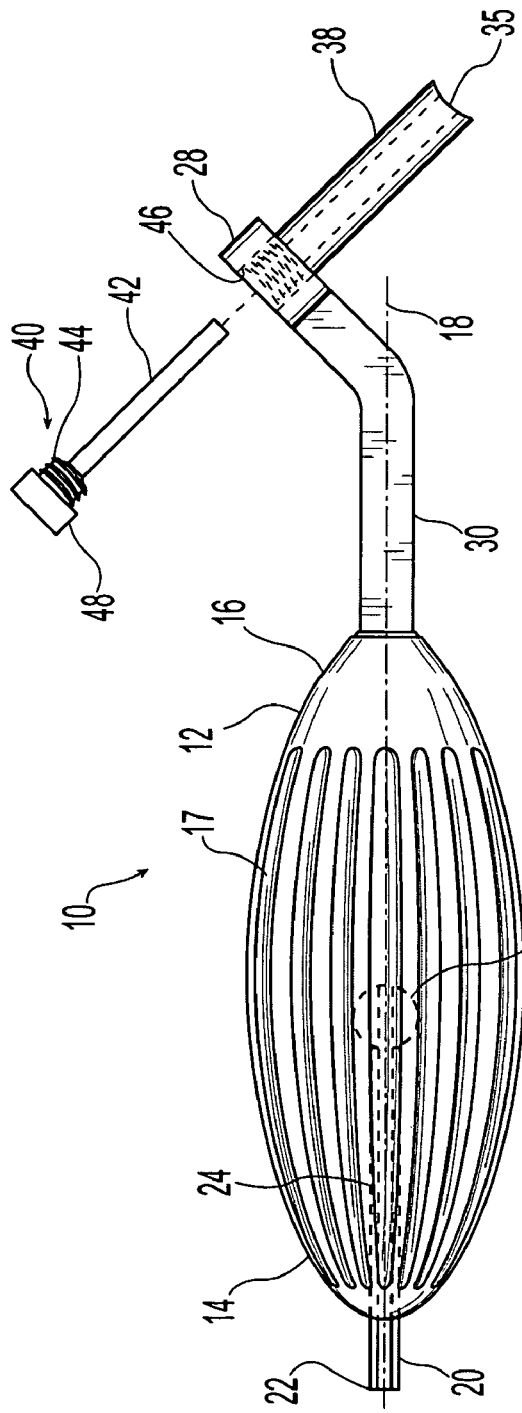
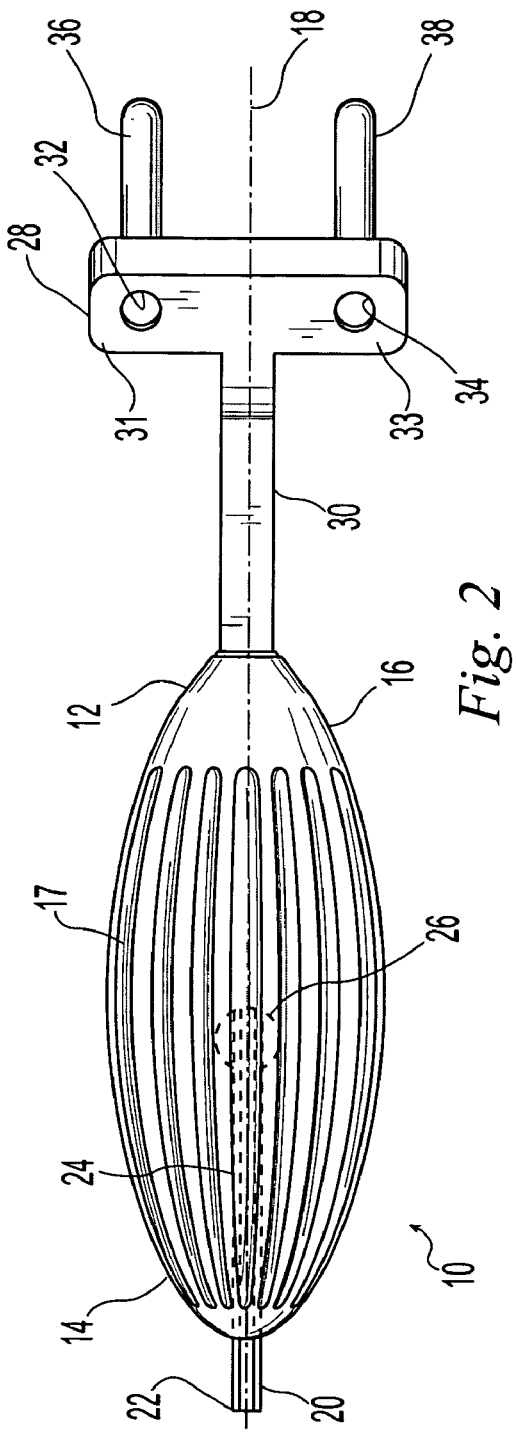
Fig. 1
Fig. 2

COMBINATION TARGETING GUIDE AND DRIVER INSTRUMENT FOR USE IN ORTHOPAEDIC SURGICAL PROCEDURES

BACKGROUND

The present invention relates to instruments for use in orthopaedic procedures. More particularly, the present invention relates to targeting guide and screw tightening instruments for use in orthopaedic procedures.

Various orthopaedic procedures require drilling holes in bones and turning screws, bolts, nuts, and adjustment mechanisms. For example, external fracture fixation has been used for many years to achieve reduction of bone fractures and maintain the reduction while healing occurs. In this procedure, pins are placed transcutaneously into the bone on both sides of the fracture. Placement of the pins is facilitated by a targeting guide. Once the pins are placed, an external fixation device is attached to the pins and adjusted to reduce the fracture. The external fixation device may include clamping mechanisms, adjustable ball joints, axial length adjustors, angle adjustors, and other mechanisms that allow the reduction parameters to be set.

In another example, fracture plating has been a widely used method of internal fracture fixation. In this procedure, a perforated plate is placed on a fractured bone with the plate spanning the fracture. A targeting guide is used to guide the drilling of holes in the bone aligned with the holes in the plate. Screws are then driven through the plate and into the bone to reduce the fracture using a hand held screwdriver.

In another example, total joint replacement often involves drilling holes and tightening screws or adjusting instruments. For example, relining the acetabulum may include placing a metal shell in the acetabulum and securing it with screws placed through the shell and into holes drilled in the pelvic bone. The holes are typically drilled using a targeting guide and the screws inserted with a hand held screwdriver.

In such procedures, targeting guides and a variety of drivers are typically provided for locating the required holes, inserting screws, and adjusting mechanisms. The complete instrument set for a particular orthopaedic device may contain several costly and bulky instruments that must be cleaned, maintained, and stored in the hospital between surgical procedures and that occupy space in the crowded operating room environment during each procedure.

SUMMARY

The present invention provides a combination targeting guide and driver instrument for use in orthopaedic surgical procedures. The instrument includes a handle having first and second ends. The first end includes a driver for engaging a screw, bolt, adjustor, and/or other article for imparting torque. The second end includes a targeting guide having at least one guide hole for guiding a drill bit, pin, or other elongated member to a desired location on a bone. The instrument is a multifunction device reversible between a targeting guide and a driver.

In one aspect of the invention, a combination targeting guide and driver instrument is provided for use during orthopaedic surgical procedures on a bone to guide elongated members such as pins and drill bits and for imparting torque to workpieces such as screws and bolts. The instrument includes a handle having first and second ends. First means are attached to the first end for engaging a workpiece for imparting torque to the workpiece and second means are attached to the second end for guiding the elongated member to a desired location on the bone.

In another aspect of the invention, a combination targeting guide and driver instrument is provided for use during orthopaedic surgical procedures on a bone to guide elongated members such as pins and drill bits and for imparting torque to workpieces such as screws and bolts. The instrument includes a handle having first and second ends. A driver is attached to the first end of the handle for engaging a workpiece for imparting torque to the workpiece. A targeting guide is attached to the second end of the handle, the targeting guide having at least one guide hole for guiding the elongated member to a desired location on the bone.

In another aspect of the invention, a method is provided for guiding elongated members such as pins and drill bits and for imparting torque to workpieces such as screws and bolts during an orthopaedic procedure. The method includes providing a combination instrument comprising a handle having first and second ends; a driver attached to the first end of the handle for engaging a workpiece for imparting torque to the workpiece; and a targeting guide attached to the second end of the handle, the targeting guide having at least one guide hole for guiding an elongated member a desired location on a bone; gripping the instrument with the targeting guide facing forward for use; positioning the targeting guide adjacent a bone; guiding an elongated member to a desired location on a bone with the targeting guide; reversing the instrument so that the driver faces forward for use; and rotating a screw with the driver.

BRIEF DESCRIPTION OF THE DRAWINGS

Various examples the present invention will be discussed with reference to the appended drawings. These drawings depict only illustrative examples of the invention and are not to be considered limiting of its scope.

FIG. 1 is a side plan view of an illustrative instrument according to the present invention showing an optional sizing insert exploded away from the instrument;

FIG. 2 is a top plan view of the instrument of FIG. 1 shown without the sizing insert for clarity.

DESCRIPTION OF THE ILLUSTRATED EMBODIMENTS

Figure 3:
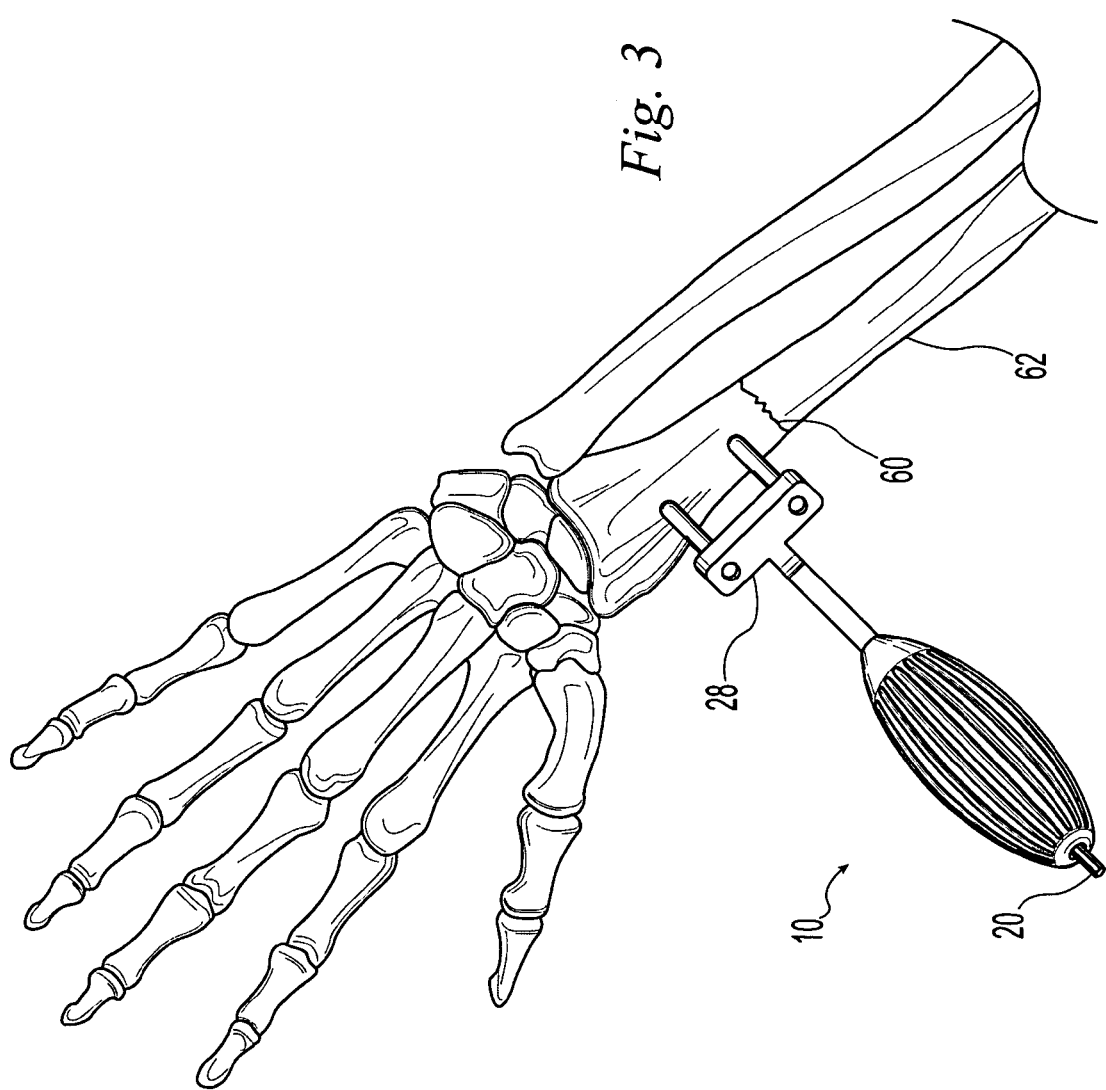
FIG. 3 is a perspective view of the instrument of FIG. 1 positioned on a bone as it would be used to position transcutaneous fixation pins.

The illustrative example of FIGS. 1-3 depicts a combination targeting guide and driver instrument 10 for use with an external fixation device. However, it will be understood by those skilled in the art that this application is illustrative only and that the instrument is usable in other applications and that modifications may be made to the device within the scope of the invention.

The instrument 10 includes a handle 12 having first and second ends 14, 16 and a longitudinal axis 18 extending from the first end 14 to the second end 16. The handle 12 has a generally circular cross section perpendicular to the axis and an elliptical longitudinal shape. The shape of the handle 12 permits it to be gripped with equal security and comfort in both a first end 14 forward position and a second end 16 forward position to facilitate reversal of the instrument for use of either end. Longitudinal grooves or scallops 17 are spaced circumferentially around the handle 12 to provide a positive interdigitating grip with a user's hand. While an exemplary handle 12 configuration has been shown, other configurations are also within the scope of the invention. For example, the handle 12 may be flat, polygonal, round, elliptical, and/or other suitable cross section. It may be flat, polygonal, cylindrical, conical, elliptical, and/or otherwise longitudinally shaped. The handle 12 may be smooth, stippled, knurled, grooved, scalloped and/or otherwise formed for a desired degree of positive gripping.

The first end 14 of the handle 12 includes a driver 20 having an engagement end 22 and an attachment portion 24. The engagement end 22 is in the form of a hexagonal rod extending outwardly from the handle 12 along the handle axis 18. However, other forms for the engagement end 22 are contemplated. For example, the driver 20 may have a male or female engagement end 22 and may be of a flat blade, triangular, square, hexagonal, Phillips, Torx®, and/or other configuration. The illustrative attachment portion 24 is embedded in the handle 12 and has the same hexagonal shape as the engagement end 22 to resist rotation relative to the handle 12. An enlarged end 26 in the form of circular, perpendicular fins further resists rotation of the driver 20 and resists axial translation of the driver 20 relative to the handle 12.

The second end 16 of the handle 12 is connected to a targeting guide 28 for guiding a drill bit, pin, or other elongated member to a desired location on a bone. The targeting guide 28 is mounted on an extension 30 projecting from the handle 12 such that the targeting guide 28 is spaced from the handle 12. The extension 30 projects along the handle axis 18 for a first predetermined distance and then bends outwardly away from the axis 18 for a second predetermined distance such that the targeting guide 28 is offset from the axis 18 in one plane. In the illustrative example, the extension 30 bends through an angle of approximately 45° in one plane. However, the extension 30 may be straight or it may bend in one or more planes at any desired angle. The targeting guide 28 is elongated perpendicular to the handle axis 18 to extend between first and second ends 31, 33 offset on opposite sides of the handle axis 18. The targeting guide 28 includes at least one guide hole 32 for receiving a drill bit, pin, or other elongated member and directing it toward the bone. In the embodiment of FIG. 2, the targeting guide 28 includes two guide holes 32, 34 formed through the first and second ends 31, 33. The targeting guide 28 preferably includes at least one guide hole extension tube 36 extending from the targeting guide 28 along the guide hole 32 axis to provide an elongated bearing surface for supporting the elongated member being guided. In the embodiment of FIG. 2, the targeting guide includes two hole extension tubes 36, 38 extending from the targeting guide 28 along the guide hole 32, 34 axes. The end 35 of each tube 36, 38 is scalloped to fit the contours of an elongated bone to facilitate secure placement of the tubes 36, 38 on the bone. While an exemplary targeting guide 28 configuration has been shown, other configurations are also within the scope of the invention. For example, the targeting guide may include one or a plurality of guide holes and they may be parallel, perpendicular, and/or transverse to the handle axis 18. The one or more holes may be in-line with and/or radially offset from the handle axis 18.

Sizing inserts 40 are provided to change the diameter of the guide holes 32, 34. Each sizing insert 40 includes a tube 42 having an outer diameter sized to fit within the guide holes 32, 34 and guide hole extension tubes 36, 38 and an inner diameter sized to receive the elongated member. A threaded portion 44 of the sizing insert 40 threads into a corresponding threaded portion 46 of the guide holes 32, 34. An enlarged collar 48 at one end of the sizing insert 40 facilitates gripping and turning the sizing insert 40 to screw it into the guide holes 32, 34.

The instrument 10 may be made by a variety of methods and of a variety of materials. For example the instrument 10 may be cast, machined, compression molded, injection molded, blow molded, stamped, punched and/or otherwise formed. The instrument 10 may made of metals, polymers, and/or other suitable materials. The instrument 10 may be made as a single piece or as an assembly. For example, in the illustrative example, the driver 20 and guide hole extensions 36, 38 are made of a metal such as aluminum or stainless steel. The handle 12 and extension 30 are blow molded from a glass-filled polymer, such as polyester, around the driver 20 and guide hole extensions 38 such that the driver and guide hole extensions 36, 38 are embedded in the handle 12 and extension 30. The illustrative construction results in an instrument 10 that is light weight, low cost, and space saving due to the combined function of the targeting guide 28 and driver 20. The instrument may be made sufficiently inexpensively that it may be provided as a disposable instrument included with each orthopaedic device with which it is to be used. For example, an external fixation device may be provided packaged with the disposable combination instrument 10. By making the instrument disposable, further cost savings may be realized by making the instrument 10 of materials that are sufficiently durable for a single procedure but that are less expensive than materials capable of repeated use and resterilization. Cost savings are also realized by eliminating hospital instrument tray storage, resterilization, and instrument maintenance.

A variety of methods may be performed with the illustrative instrument 10. FIG. 3 illustrates a fracture 60 of the radius 62 of the human forearm. The instrument 10 is shown in position to guide fixation pins into the bone on one side of the fracture 60. The instrument 10 would then be used to place fixation pins on the opposite side of the fracture 60. An external fixator would then be assembled to the pins and the driver 20 would be used to adjust and tighten the fixator. In another example, the targeting guide 28 is positioned adjacent a bone with the guide hole extension tubes 36, 38 pressed against the bone. A drill bit is extended through the guide holes 32, 34 and extension tubes 36, 38 and into the bone to form bone holes. The targeting guide is then removed from the bone and reversed to drive a screw with the driver 20. In another example, a sizing insert 40 may be used to reduce the diameter of the guide holes 32, 34 to guide a reduced size drill bit. The drill bit and sizing insert 40 may then be removed and pins or screws may be inserted through the guide holes 32, 34 to guide them into the bone holes.

It will be understood by those skilled in the art that the foregoing has described illustrative embodiments of the present invention and that variations may be made to these embodiments without departing from the spirit and scope of the invention defined by the appended claims.

What is claimed is:

1. A method for guiding at least one elongated member and for imparting torque to a fastener during an orthopaedic procedure, the method comprising:
   providing a combination instrument comprising:
      a handle having first and second ends;
      a driver attached to the first end of the handle for engaging and for imparting torque to the fastener; and
      a targeting guide attached to the second end of the handle, the targeting guide having at least one guide hole for guiding at least one elongated member to a desired location on a bone;
   gripping the instrument with the targeting guide facing forward for use;
   positioning the targeting guide adjacent a bone;

guiding the at least one elongated member to a desired location on the bone with the targeting guide;

reversing the instrument so that the driver faces forward for use;

engaging the fastener with the driver; and imparting torque to the fastener.

2. The method of claim 1 wherein the elongated member guided by the targeting guide is a transcutaneous external fixator pin and the fastener is part of a clamping mechanism on an external fixator, the method further comprising:

using the targeting guide to place transcutaneous external fixator pins on opposite sides of a fracture; and using the driver to tighten the clamping mechanism onto the pin.

3. The method of claim 1 wherein the handle has an axis and a generally circular cross section perpendicular to the axis and an elliptical longitudinal shape such that the handle may be gripped with equal security and comfort with both the targeting guide facing forward for use and the driver facing forward for use.

4. The method of claim 1 wherein the targeting guide further includes at least one guide hole extension tube extending from the targeting guide along a guide hole axis to provide an elongated bearing surface for supporting the elongated member, the end of the tube being scalloped to fit the contours of the bone, and wherein the guiding step comprises placing the scalloped end of the tube against the bone.

5. The method of claim 4 wherein the targeting guide includes at least one sizing insert to change the diameter of the guide hole, the sizing insert including a tube having an outer diameter sized to fit within the guide hole and guide hole extension tube and an inner diameter sized to guide the elongated member, and wherein the guiding step comprises guiding the elongated member through the sizing insert.

6. The method of claim 1 wherein the combination instrument comprises an extension projecting from the handle, the targeting guide being mounted on said extension such that the targeting guide is spaced from the handle, the extension projecting along an axis of the handle for a first predetermined distance and then bending outwardly away from the axis for a second predetermined distance such that the targeting guide is offset from the axis in one planet.

7. The method of claim 1 wherein the driver comprises an engagement end extending outwardly from the handle and an attachment portion embedded in the handle, the attachment portion having a non-circular cross section to resist rotation relative to the handle during the imparting torque step, the attachment portion further having an enlarged end embedded in the handle to resist axial translation of the driver relative to the handle.

\* \* \* \* \*